(12) United States Patent
Davis

(10) Patent No.: US 9,265,721 B2
(45) Date of Patent: *Feb. 23, 2016

(54) COMPOSITION FOR PROMOTING VASCULAR SMOOTH MUSCLE RELAXATION

(75) Inventor: Adrian Francis Davis, Dorking (GB)

(73) Assignee: FUTURA MEDICAL DEVELOPMENTS LIMITED, Guildford Surrey (GB)

(*) Notice: Subject to any disclaimer, the term of this patent is extended or adjusted under 35 U.S.C. 154(b) by 0 days.

This patent is subject to a terminal disclaimer.

(21) Appl. No.: 12/223,583

(22) PCT Filed: Jan. 23, 2007

(86) PCT No.: PCT/GB2007/000212
§ 371 (c)(1),
(2), (4) Date: Aug. 4, 2008

(87) PCT Pub. No.: WO2007/088327
PCT Pub. Date: Aug. 9, 2007

(65) Prior Publication Data
US 2009/0018214 A1     Jan. 15, 2009

(30) Foreign Application Priority Data

Feb. 3, 2006   (GB) .................................. 0602224.8

(51) Int. Cl.
| | | |
|---|---|---|
| *A61K 31/14* | (2006.01) | |
| *A61K 9/00* | (2006.01) | |
| *A61K 9/14* | (2006.01) | |
| *A61K 31/21* | (2006.01) | |
| *A61K 45/06* | (2006.01) | |
| *A61K 47/10* | (2006.01) | |
| *A61K 47/32* | (2006.01) | |

(52) U.S. Cl.
CPC ............ *A61K 9/0014* (2013.01); *A61K 9/0034* (2013.01); *A61K 9/145* (2013.01); *A61K 31/21* (2013.01); *A61K 45/06* (2013.01); *A61K 47/10* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 3,155,574 A | 11/1964 | Silson et al. | |
| 4,481,220 A | 11/1984 | Giesselmann et al. | |
| 4,615,699 A | 10/1986 | Gale | |
| 5,047,230 A * | 9/1991 | Nagy et al. ...................... | 424/45 |
| 5,370,862 A * | 12/1994 | Klokkers-Bethke et al. ... | 424/47 |
| 5,698,589 A | 12/1997 | Allen | |
| 5,744,124 A * | 4/1998 | Klokkers-Bethke et al. ... | 424/47 |
| 5,807,569 A * | 9/1998 | Davis et al. ................... | 424/449 |
| 5,932,227 A | 8/1999 | Higo et al. | |

FOREIGN PATENT DOCUMENTS

| | | | | |
|---|---|---|---|---|
| EP | 0 310 910 | * | 4/1989 | ............. A61K 31/21 |
| WO | 99/38506 A2 | | 8/1999 | |

OTHER PUBLICATIONS

Fitch (Am Heart J 71:417-419, 1966).*
International Search Report in PCT/GB2007/000212.
Written Opinion of the International Searching Authority in PCT/GB2007/000212.

* cited by examiner

*Primary Examiner* — Craig Ricci
(74) *Attorney, Agent, or Firm* — Gianna Julian-Arnold; Saul Ewing LLP

(57) ABSTRACT

A composition for topical application to a part of the body comprises a local anaesthetic and optionally a vasodilator as active ingredient dissolved in a blend of volatile and non-volatile solvents of different solvating capacities for the active ingredient. The vasodilator may comprise glyceryl trinitrate and the local anaesthetic may comprises an anaesthetic of the aminoamide or aminoester type. The volatile solvent may comprise a mixture of water with a $C_1$-$C_5$ alcohol and the non-volatile solvent may comprise a polyhydric alcohol and optionally a glycol. A low-concentration vasodilator-containing composition is also described. The compositions allow a "virtual injection" of the active ingredient to be delivered transdermally without general systemic uptake.

12 Claims, 3 Drawing Sheets

*Residual activity 22.5

COMPOSITION FOR PROMOTING VASCULAR SMOOTH MUSCLE RELAXATION

This invention relates to the treatment or amelioration of conditions susceptible to vascular smooth muscle relaxation, such conditions including especially angina and sexual dysfunction.

One facet of sexual dysfunction is erectile dysfunction—that is, the failure to achieve or sustain an erection of the penis in males sufficient to enable sexual intercourse to take place—which is an increasing or increasingly recognised problem. Females also can suffer from sexual dysfunction in that the sensory genital regions such as the clitoris and periclitoral regions do not become fully engorged during sexual activity to enable optimum sexual satisfaction or fulfillment to be experienced, due to arousal and/or desire disorders. Angina is experienced when the coronary blood flow is insufficient to meet the heart's metabolic requirements. Both conditions can be treated or ameliorated by the topical application of a vasodilator-containing composition, glyceryl trinitrate or nitroglycerin being a commonly-used vasodilator for this purpose.

For treatment of erectile dysfunction, the glyceryl trinitrate (GTN) or other vasodilator, on application to erectile genitalia and absorption through the skin, results in a local enhancement in blood supply to the organ and hence to a better quality of erection. One such composition is described in WO 99/38506 and contains lanolin as a lubricant and as a skin penetration enhancement material. It has been found that such compositions result in use in a surprisingly low incidence of headache (a known side effect of GTN when used, for example, for the treatment of angina). However, although such compositions may be effective, significant absorption of GTN into the blood stream may occur resulting in systemic adverse effects and the potential for drug interactions.

A further composition, especially for use in the treatment of angina, is described in U.S. Pat. No. 5,047,230 as an aerosol composition containing no propellant gas and comprising GTN as active ingredient dispersed in 51-90% by weight of a $C_{2-4}$ aliphatic alcohol, preferably ethanol, 10-49% by weight of a polyalkyleneglycol having 2 or 3 carbon atoms in the alkylene moiety, and/or a $C_{2-8}$ alcohol having two or three hydroxyl groups. The high alcohol concentration results, by virtue of exerting a direct effect on the skin barrier, in better and faster absorption of the active ingredient. However, for application to the male or female genitalia, such high alcohol concentrations cause a burning or stinging sensation and are therefore unacceptable.

Ideally, for treatment of erectile dysfunction in males, targeted delivery to the penis is required whereby local, regional, effects of the drug are enjoyed but such that systemic distribution and subsequent systemic effects are avoided. Although such an ideal solution is unachievable in practice because at least some systemic uptake is inevitable following topical administration, use of low doses of GTN delivered as a "virtual injection" would approximate to the ideal state, provided that transdermal or percutaneous absorption was sufficiently rapid. Once tumescence and erection is achieved by pharmacological intervention, physiological block of the venous return of blood will self sustain the erection. The requirements to provide a composition from which sufficient active ingredient will be absorbed for initiating the intended effect, while maintaining the dose at a low level to avoid subsequent systemic effects, are thus to some extent mutually conflicting. Similarly in females with sexual dysfunction, a rapid and targeted delivery to the vagina and clitoral region is required so that effective levels of drug are delivered to these specific regions through topical application in order to keep systemic levels to a minimum.

Many technologies have been described to increase percutaneous penetration. Amongst these it is well known to saturate the drug in the formulation so as to optimise partitioning into and thus solubility in the stratum corneum barrier of the skin and thus also to optimise percutaneous transport. For the vast majority of drugs, this results in zero-order steady-state maximum input into the skin over the dosing period. In part this zero order is due to the extent of absorption being so low, compared to the dose applied, that no effective depletion of the saturated, optimum, state occurs. However, with drugs that are efficiently absorbed and especially when the drug is applied at a low dose, as in the case of a "virtual injection" as described above, rapid depletion significantly reduces the degree of saturation, referred to as the chemical activity state, of the active ingredient in the formulation and thus reduces the transport rate.

Premature ejaculation is another male sexual dysfunctional condition characterised by the inability to delay ejaculation until it is mutually desirable for both partners. The condition results in frustration for both sexual partners and can, in extreme cases, result in an inhibition of relationships and even in impotence. Various mental and physical procedures are advocated for avoiding premature ejaculation, and a pharmacological treatment is by administration of antidepressants. However, such compositions require to be administered approximately four hours before intercourse takes place which requires a somewhat prescriptive approach to sexual activity. It is also possible to treat the condition by application to the penis of a composition including a local anaesthetic, in order to reduce the nerve sensations transmitted from the penis and which are thought to result in orgasm. However, to the extent that such nervous sensations are partially instrumental in maintaining an erection, the application of such compositions can have the unintended consequence of causing or exacerbating erectile dysfunction and in any event the delay in ejaculation resulting from application of a local anaesthetic is not particularly marked.

It is therefore an object of the present invention to provide a composition which, on being applied to the skin, delivers a "virtual injection" of active ingredient to the target site. The invention maintains the degree of saturation and the chemical activity state of active ingredient therein essentially throughout the absorption process to provide a continuing driving force as percutaneous absorption takes place. It is also an object to provide a composition which, while providing for continuing percutaneous absorption of active ingredient, also provides a low half-life of active ingredient in the bloodstream, thus resulting in rapid elimination so as not to accumulate in the systemic circulation.

In one aspect, the invention provides a composition for topical application to a part of the body, the composition comprising a vasodilator and optionally a local anaesthetic as active ingredient dissolved in a blend of volatile and non-volatile solvents of different solvating capacities for the active ingredient.

The active ingredient is present in the composition as formulated preferably at a concentration at or slightly below saturation, whereby evaporation of the volatile solvent in use will maintain the active ingredient at saturated or super-saturated concentrations in the residue.

Preferably, the non-volatile solvent has the lower solvating capacity, compared with the volatile solvent.

The vasodilator preferably comprises glyceryl trinitrate and the local anaesthetic preferably comprises anaesthetics of the aminoamide or aminoester type, for example lidocaine, benzocaine, prilocaine and the like.

In use and on application to an affected body part such as erectile tissue, for example the penis, by hand, the composition will form a thin film over the glans, thereby providing an extended surface area over which the composition is supported and which, in combination with body warmth, will cause the volatile solvent component to evaporate. The active ingredient will thus become saturated or supersaturated in the solvent remaining and, as the active ingredient passes through the skin and is absorbed in the bloodstream, and thus becomes depleted in the residual composition, continuing evaporation of volatile solvent will maintain the active ingredient substantially at saturation or supersaturation level in the residual composition throughout the major part of the absorption phase, thereby maximising absorption levels but at a moderate dosage level.

In another aspect, therefore, the invention provides a method for the treatment or amelioration of a condition susceptible to vascular smooth muscle relaxation, or premature ejaculation, the method comprising topical application to an affected body part of a composition comprising a vasodilator and/or a local anaesthetic as active ingredient dissolved in a blend of volatile and non-volatile solvents of different solvating capacities for the active ingredient, and allowing volatile solvent to evaporate.

Compositions according to the invention may be supplied in a tube or other container but preferably are provided in unit-dosage form. In unit-dosage form, the dose of vasodilator as active ingredient should be as low as possible consistent with the desirability of maintaining an effective amount in the residual composition, generally up to 5 mg, preferably 2.5 mg or less, for example 1.0 mg or even 0.5 mg. Thus, for a nominal concentration of vasodilator of 1.0% by weight in the composition as formulated, a unit dose of 100 mg would provide 1.0 mg of vasodilator. However, even more preferably, the effectiveness of the invention in enabling absorption to be maintained as evaporation of solvent takes place allows even lower dosages of up to 0.25 mg, for example 0.05 to 0.25 mg of glyceryl trinitrate in a unit dose of 300 mg of the composition, that is, from 0.0167 to 0.083% by weight, say from 0.015 to 0.1% by weight, to be used. A preferred low-dosage concentration range, for optimizing efficacy while minimising systemic uptake, is 0.04 to 0.08%, for example 0.05%. For anaesthetics, the dosage concentration range may be 0.01 to 1.0% by weight, preferably 0.015 to 0.5% by weight.

In compositions according to the invention, the solvents are water-miscible and the consistency is preferably that of a spreadable gel or a cream. For reasons of aesthetic consumer acceptability, the gel is preferably relatively clear and colourless and has an agreeable feel on the skin, without being gloopy or leaving gloopy residues as absorption proceeds.

The volatile solvent component in compositions according to the invention preferably comprises a mixture of water with a low molecular weight alcohol to enhance the solvating power and to lower the boiling point. A suitable alcohol comprises ethanol, for reasons of cost, availability, volatility and toxicity, but other lower alcohols containing up to five carbon atoms may be used, preferably isopropanol, as an alternative or additionally to ethanol. The water and alcohol solvent may be present in a ratio from 0.5:1 to 2.5:1, preferably 0.7:1 to 2.0:1, by weight. For example, using ethanol as the alcohol, the percentages by weight may be 40% water, 30% ethanol (1.3:1) or 29% water, 36% ethanol (0.8:1), the balance in each case being non-volatile solvent. In a more preferred range, the ratio would be 1:1 or higher or even more preferably 1.5:1 or higher. The alcohol should normally have a maximum concentration of 40% by weight, although lower concentrations, such as 35% or even 30% by weight, based on the total formulation, are preferred, provided that there is sufficient solvating power for the active ingredient at the intended concentration. In compositions according to the invention, it has been found that percutaneous absorption is rapid despite a low alcohol concentration, because of the effect of the solvent blend in maintaining the active ingredient concentration at saturation or supersaturation levels in the residual composition as absorption takes place.

In another aspect, the invention provides a composition for topical application to a part of the body, the composition comprising a vasodilator as active ingredient dissolved in a blend of volatile and non-volatile solvents of different solvating capacities for the active ingredient, in which the volatile solvent comprises a mixture of water and a low molecular weight alcohol in a ratio by weight of 1.6:1 to 2.5:1.

The invention also includes compositions containing only a vasodilator as active ingredient, in which the vasodilator comprises glyceryl trinitrate and is present in a concentration from 0.015 to 0.1% by weight dissolved in a mixture of water and a $C_1$-$C_5$ alcohol. Preferably, the alcohol comprises ethanol at a concentration up to 40% by weight, preferably 35% as a maximum, such as 30%. The water:ethanol ratio is preferably 1.75:1 to 2.5:1, more preferably from 1.8:1 to 2.3:1.

The non-volatile solvent, which preferably has the lower solvating capacity, is present preferably in a lower concentration than the volatile solvent, preferably from 0 to 40% by weight of the total solvent content, preferably from 5 to 30%, to optimise the concentration in the residual composition while still providing sufficient solvating power in the total composition to dissolve the required amount of active ingredient. The non-volatile solvent may comprise a polyhydric alcohol, glycerol (boiling point 290° C.) being preferred for reasons of availability and acceptability. The high-boiling alcohol may be blended with a minor amount of additional solvent to modify its properties. A suitable additional solvent comprises a glycol, for example propylene glycol, which may be present at up to 20% of the total non-volatile component, preferably up to 15%, for example 5.0% by weight or 12.5% by weight.

Where the active ingredient comprises glyceryl trinitrate, it has been found that high levels of supersaturation in the residual phase after evaporation of volatile solvents in use may be generated by selecting the solvents so as to provide a volatile solvent component allowing a saturated solubility of glyceryl trinitrate in excess of 1% with a non-volatile solvent component allowing a saturated solubility of less than 1%. However, within this requirement, it is desirable that the maximum concentration of ethanol (as the volatile co-solvent with water) should not exceed 40% of the total solvent component and that the maximum concentration of glycerol (as the primary non-volatile solvent) should not exceed 30%, although in each case these limits are not absolute and are based on anticipated user acceptance levels. In compositions according to the invention as supplied for use, glyceryl trinitrate as the vasodilator is preferably present in the total solvent system at a slightly sub-saturated concentration to allow super-saturation to occur upon loss of volatile components.

In a unit dosage formulation where the active ingredient is glyceryl trinitrate, it is preferred that water:ethanol ratio is between 1.25:1 and 1.9:1, the ethanol concentration being between 30 and 35% of the total formulation and the glycerol concentration being from 0 to 30%, more preferably 5 to 30%, even more preferably 5 to 25%. It has been found that such solvent amounts provide a saturated glyceryl trinitrate concentration of up to 1.25% with a level of saturation in the residual composition of greater than 1, with initial glyceryl trinitrate amounts between 0.25 and 2.5 mg. The unit dosage formulation may amount to 300 mg of composition.

Compositions according to the invention also optionally include additional ingredients such as agents for enhancing skin feel, for example a silicone oil composition such as Dimethicone 200; thickening or gelling agents, for example a polyacrylate-based composition such as Carbopol 937P; neutralising agents such as triethanolamine; and antimicrobial preservatives such as methyl and propylparaben.

It has been found that, based on an in vitro experimental model using a SAMCO silastic membrane to simulate skin, compositions according to the invention exhibit improved trans-dermal transport properties compared with Percutol, an available topical composition containing glyceryl trinitrate for the treatment of angina.

The invention will now be described with reference to the following experimental details, provided purely by way of example, and with reference to the accompanying drawings, of which:

The experiments provided compositions having a nominal concentration of glyceryl trinitrate of a minimum of 1% or 2% based on the total of volatile and non-volatile solvents. The solvents used were water and ethanol as the volatile component and glycerol together with propylene glycol as an optional additive as the non-volatile component. The experiments related to the use of three respective variables, firstly various ratios of 1% glyceryl trinitrate (GTN) in 57.5:42.5 water:ethanol (1.35:1) and 1% GTN in 87.5:12.5 glycerol:propylene glycol (7:1) (QS 1-QS 6); secondly GTN in various ratios of water-ethanol systems and GTN in glycerol alone (QS 7-QS 13); and thirdly GTN in various ratios of different water:ethanol systems with GTN in 95:5 glycerol:propylene glycol (QS 14-QS 18). For each experiment, the concentration of GTN remaining in the residual (non-volatile) solvent and expressed as a multiple of the saturated concentration was estimated, based on volume change and taking account of the saturated concentration in the solvent or solvent blend of the residual phase.

Figure 1:
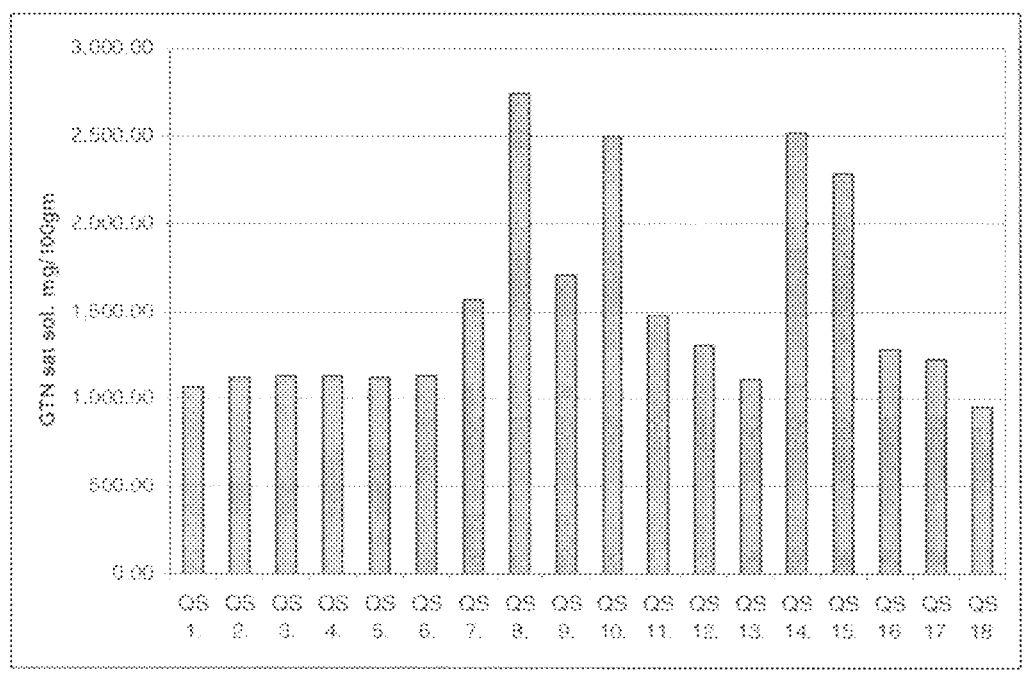
FIG. 1 is a bargraph showing comparative saturated solubility of GTN in various solvent blends.

Initially, predicted saturated concentration in the quarternary solvent blends was estimated based on experimental determinations in binary cosolvents, namely ethanol/water at different ratios and glycerol/propylene glycol at different ratios. It was predicted that the saturated concentration of GTN would be 1% in most quaternary blends or 2% in others (QS 8, QS 10, QS 14 and QS 15). FIG. 1 shows experimental data for the saturated solubility of GTN in the various quaternary and tertiary (QS 7-QS 13) blends. As illustrated, good agreement with prediction was shown by QS 1 to QS 6; QS 7 to QS 13 showed higher solubilities than predicted and QS 14 to QS 18 were also higher, albeit not to the same extent as with QS 7 to QS 13.

Table 1 shows the details of each experiment and the estimated residual concentration of GTN expressed as a multiple of the saturated concentration in the residual solvent.

TABLE 1

| Series (W-E:G-PG) | Water (%) | Ethanol (%) | Glycerol (%) | Prop Glycol (%) | Conc. Of GTN (predicted) (%), Approx. *SS (predicted) |
|---|---|---|---|---|---|
| QS 1. | 28.75 | 21.25 | 43.75 | 6.25 | (1), *2 |
| QS 2. | 31.65 | 23.375 | 39.375 | 5.625 | (1), *2.2 |
| QS 3. | 34.5 | 25.5 | 35.5 | 5.0 | (1), *2.5 |
| QS 4. | 37.375 | 27.625 | 30.625 | 4.375 | (1), *2.86 |
| QS 5. | 40.25 | 29.75 | 26.25 | 3.75 | (1), *3.33 |
| QS 6. | 43.125 | 31.875 | 21.875 | 3.125 | (1), *4 |
| QS 7. | 15.2 | 22.8 | 62 | 0 | (1), *4.24 |
| QS 8. | 25.6 | 38.4 | 36.0 | 0 | (2), *14.61 |
| QS 9. | 19.8 | 24.2 | 56.0 | 0 | (1), *4.70 |

TABLE 1-continued

| Series (W-E:G-PG) | Water (%) | Ethanol (%) | Glycerol (%) | Prop Glycol (%) | Conc. Of GTN (predicted) (%), Approx. *SS (predicted) |
|---|---|---|---|---|---|
| QS 10. | 33.3 | 40.7 | 26 | 0 | (2), *20.23 |
| QS 11. | 27.0 | 27.0 | 46 | 0 | (1), *5.72 |
| QS 12. | 42.9 | 35.1 | 22 | 0 | (1), *11.94 |
| QS 13. | 39.55 | 30.45 | 30 | 0 | (1), *8.76 |
| QS 14. | 21.6 | 32.4 | 43.7 | 2.3 | (2), *5.35 |
| QS 15. | 29.25 | 35.75 | 33.25 | 1.75 | (2), *7.03 |
| QS 16. | 15. | 15. | 66.50 | 3.50 | (1), *1.76 |
| QS 17. | 30.25 | 24.75 | 41.75 | 2.25 | (1), *2.77 |
| QS 18. | 41.125 | 28.875 | 28.5 | 1.5 | (1), *4.1 |

Note
that QS 8, 10, 14 and 15 had a predicted 2% GTN concentration whereas the remainder had a 1% concentration.

From the above results, it is seen that QS 4, QS 5, QS 6, QS 12, QS 13, QS 15 and QS 18 provide promising results in terms of supersaturation in the residual solvent and are within the requirements for ethanol and glycerol limits, respectively. QS 3, QS 8 and QS 10 are also identified as of interest, although QS 10 has a concentration of ethanol which is higher than considered desirable. The remainder, although showing enhanced levels of supersaturation in the residual solvent, may be unacceptable because of the glycerol levels.

The following Table 2 shows the formulation of compositions using solvent blends QS 6 and QS 13, in percentages by weight.

TABLE 2

| Ingredient | QS 6. | QS 13. |
|---|---|---|
| GTN (10% on lactose) | 10 | 10 |
| Water | 38.25 | 35.08 |
| Ethanol | 28.97 | 27.01 |
| Glycerol | 19.41 | 26.61 |
| Propyleneplycol | 2.77 | — |
| Dimethicone 200 | — | — |
| Carbopol 937P | 1.00 | 1.00 |
| Triethanolamine | 0.20 | 0.20 |
| Propylparaben | 0.10 | 0.10 |

Figure 2:
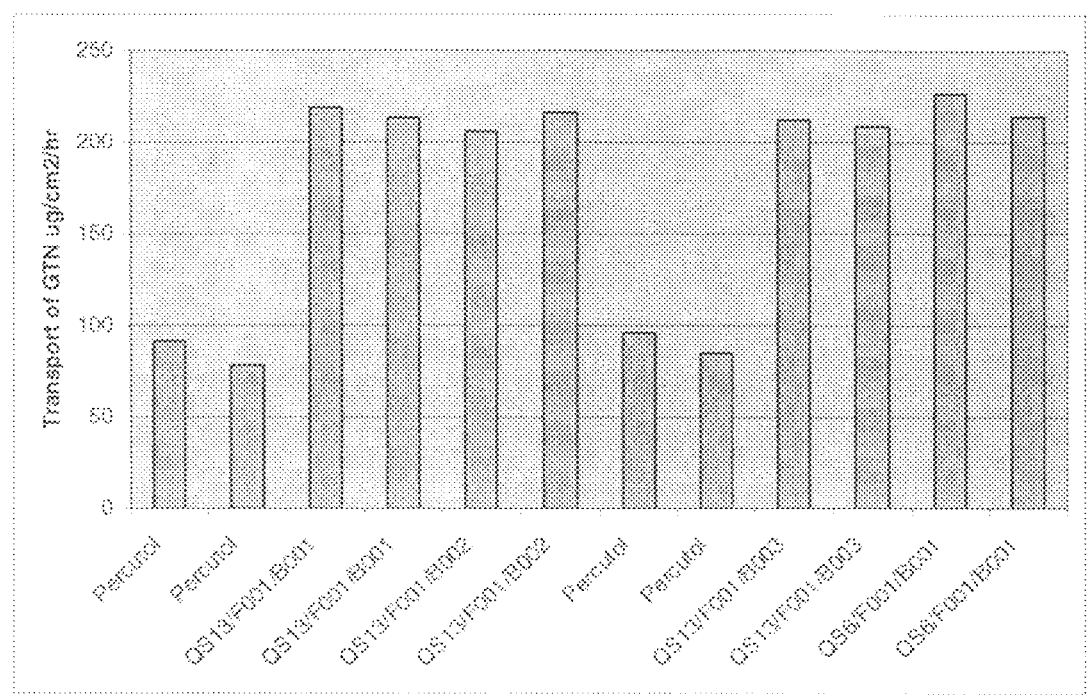
FIG. 2 is a bargraph showing in vitro transport of compositions according to the invention compared with Percutol.

To evaluate skin absorption, the experimental systems QS 6 and QS 13 were compared with Percutol in an experimental model in which diffusion of GTN from the test solvent through a SAMCO Silastic membrane into a buffered phosphate receptor fluid was assessed over a period of one hour. All experimental systems performed appreciably (between twice and three times) better than Percutol as shown in accompanying FIG. 2.

However, such in vitro tests, which are difficult to conduct under finite dose, thin-film conditions, may not be fully predictive of in vivo performance. Thus, compositions according to the present invention have also been evaluated in a Phase I clinical trial in comparison with a formulation according to WO99/38506. Results are presented in the following Table 3 for peak systemic levels ($C_{max}$), time taken to achieve peak systemic levels ($T_{max}$) and plasma half-life ($t_{1/2}$).

TABLE 3

| Formulation | GTN dose (mg) | $C_{max}$ (pg/ml) | $T_{max}$ (minutes) | $t_{1/2}$ (minutes) |
|---|---|---|---|---|
| WO99/38506 | 20.0 | 949.64 | 25.94 | 96.31 |
| Current | 1.0 | 1267.50 | 14.67 | 8.53 |

As can be seen, peak systemic levels for the current formulation, at a dose of 1 mg, are significantly higher than for the lanolin-containing composition at a dose of 20 mg. The shorter time taken to achieve the peak systemic levels is indicative of more rapid GTN absorption, despite the lower dose. The significantly shorter half-life indicates rapid absorption and rapid elimination of GTN. The current formulation is estimated to be approximately 25-fold more effective than the lanolin-containing formulation at delivery through the membrane of the glans penis.

Table 4 illustrates further formulations where the glyceryl trinitrate is added as a 5% (by weight) solution in ethanol and glycerol is the only non-volatile solvent. The amounts of the ingredients are in gm/1000 gm and of glyceryl trinitrate are also expressed (between 0.01 and 11.0 mg) as the amount in a unit dose of 300 mg and as a percentage by weight.

TABLE 4

| | QS 20 gel formulation | | | | | | | | |
|---|---|---|---|---|---|---|---|---|---|
| Ingredients | 0.00 mg 0.0% | 0.01 mg 0.0033% | 0.025 mg 0.0083% | 0/050 mg 0.0167% | 0/075 mg 0.025% | 0.10 mg 0.033% | 0.25 mg 0.083% | 0.50 mg 0.167% | 1.00 mg 0.33% |
| 5% w/w GTN in Ethanol BP | 0.0 | 0.67 | 1.67 | 3.34 | 5.00 | 6.67 | 16.67 | 33.34 | 66.67 |
| Water | 577.2 | 577.2 | 577.2 | 577.2 | 577.2 | 577.2 | 577.2 | 577.2 | 577.2 |
| Ethanol | 310.8 | 310.16 | 309.21 | 307.63 | 306.05 | 304.46 | 294.96 | 279.13 | 247.4 |
| Glycerol | 100.0 | 100.0 | 100.0 | 100.0 | 100.0 | 100.0 | 100.0 | 100.0 | 100.0 |
| Carbopol 934P | 10.0 | 10.0 | 10.0 | 10.0 | 10.0 | 10.0 | 10.0 | 10.0 | 10.0 |
| Triethanol-amine NF | 2.0 | 2.0 | 2.0 | 2.0 | 2.0 | 2.0 | 2.0 | 2.0 | 2.0 |
| Total | 1000.0 | 1000.03 | 1000.08 | 1000.17 | 1000.25 | 1000.33 | 1000.83 | 1001.67 | 1003 |

Table 5 illustrates the QS13, QS19 and QS20 solvent systems

TABLE 5

| Series (W-E:G-PG) | W-E donor | G-PG donor | Ratio W-E:G-PG | Water (%) | Ethanol (%) | Glycerol (%) | Prop Glycol (%) |
|---|---|---|---|---|---|---|---|
| QS13 | 56.5:43.5 | 100G | 70:30 | 39.55 | 30.45 | 30 | 0 |
| QS19 | 60:40 | 100G | 80:20 | 48 | 32 | 20 | 0 |
| QS20 | 65:35 | 100G | 90:10 | 58.5 | 31.5 | 10 | 0 |

It was determined experimentally that gylceryl trinitrate has a saturated concentration in the QS13 solvent system of 1.11% GTN, whereby 1% GTN represents a slightly sub-saturated solution, 0.82% GTN in the QS19 system and 0.48% GTN in the QS20 system.

Figure 3:
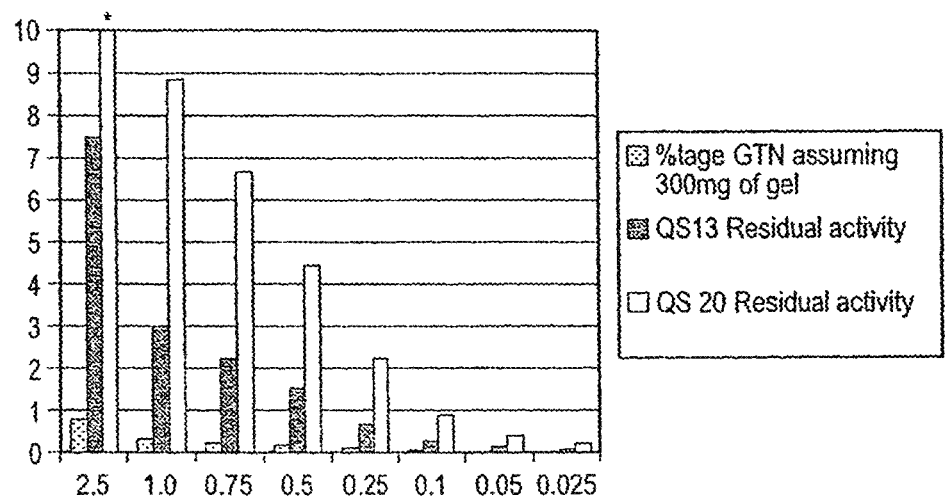
FIGS. 3 and 4 show graphically the residual activity of compositions according to the invention.
Figure 4:
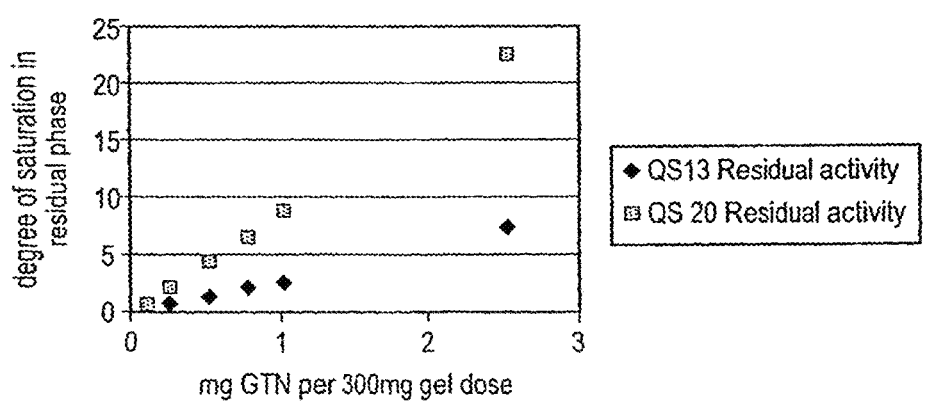

FIG. 3 is a bargraph comparing QS13 and QS20 formulations each containing various amounts of GTN in terms of residual activity—that is, the degree of saturation in the residual composition. FIG. 4 shows the residual activity graphically.

As can be seen, the QS20 solvent system containing 10% glycerol enables residual activities of almost 10 to be achieved at a GTN dose of 11.0 mg, compared with QS13 (30% glycerol) which requires a GTN dose of 2.5 mg to achieve a residual activity of 7.5. Both systems had ethanol concentrations of approximately 30%. Although the solvent system of QS20 was not as good as QS13 in terms of the saturated concentration of GTN, nevertheless it enabled a sufficient amount to be dissolved to provide for better residual activity.

Tables 6 and 7 illustrate further formulations with different solvent blends, amounts of ingredients being expressed on the same basis as for Table 4. In Tables 6 and 7, the relative concentration of non-volatile solvent is higher than in Table 5; the compositions of Table 6 use glycerol as the non-volatile solvent and the compositions of Table 7 use a blend of glycerol and propylene glycol.

In Tables 5, 6 and 7, concentrations of glyceryl trinitrate vary from 0.0033 to 0.33% (Table 5), 0.005 to 0.5% (Table 6) and 0.0083 to 0.83% (Table 7). Concentrations below 0.02% are likely to be too low to show adequate efficacy, however.

TABLE 6

| | QS 21 gel formulation | | | | | | | | |
|---|---|---|---|---|---|---|---|---|---|
| Ingredients | 0.00 mg 0.0% | 0.015 mg 0.0050% | 0.038 mg 0.0127% | 0/075 mg 0.025% | 0.11 mg 0.037% | 0.15 mg 0.050% | 0.38 mg 0.127% | 0.75 mg 0.25% | 1.50 mg 0.50% |
| 5% w/w GTN in Ethanol BP | 0.0 | 1.00 | 2.54 | 5.00 | 7.4 | 10.00 | 25.40 | 50.00 | 100.00 |
| Water | 357.8 | 357.8 | 357.8 | 357.8 | 357.8 | 357.8 | 357.8 | 357.8 | 357.8 |

TABLE 6-continued

| | QS 21 gel formulation | | | | | | | | |
|---|---|---|---|---|---|---|---|---|---|
| Ingredients | 0.00 mg 0.0% | 0.015 mg 0.0050% | 0.038 mg 0.0127% | 0/075 mg 0.025% | 0.11 mg 0.037% | 0.15 mg 0.050% | 0.38 mg 0.127% | 0.75 mg 0.25% | 1.50 mg 0.50% |
| Ethanol | 330.2 | 329.25 | 327.79 | 325.45 | 323.17 | 320.70 | 306.07 | 282.70 | 235.20 |
| Glycerol | 300.0 | 300.0 | 300.0 | 300.0 | 300.0 | 300.0 | 300.0 | 300.0 | 300.0 |
| Carbopol 934P | 10.0 | 10.0 | 10.0 | 10.0 | 10.0 | 10.0 | 10.0 | 10.0 | 10.0 |
| Triethanol-amine NF | 2.0 | 2.0 | 2.0 | 2.0 | 2.0 | 2.0 | 2.0 | 2.0 | 2.0 |
| Total | 1000.0 | 1000.05 | 1000.13 | 1000.25 | 1000.37 | 1000.5 | 1000.27 | 1002.5 | 1005.00 |

TABLE 7

| | QS 22 gel formulation | | | | | | | | |
|---|---|---|---|---|---|---|---|---|---|
| Ingredients | 0.00 mg 0.0% | 0.025 mg 0.0033% | 0.06 mg 0.02% | 0.12 mg 0.04% | 0.18 mg 0.06% | 0.25 mg 0.083% | 0.60 mg 0.020% | 1.20 mg 0.40% | 2.50 mg 0.83% |
| 5% w/w GTN in Ethanol BP | 0.0 | 1.66 | 4.00 | 8.00 | 12.00 | 16.60 | 40.00 | 80.00 | 166.00 |
| Water | 357.8 | 357.8 | 357.8 | 357.8 | 357.8 | 357.8 | 357.8 | 357.8 | 357.8 |
| Ethanol | 330.2 | 328.62 | 326.4 | 322.6 | 318.8 | 314.43 | 292.2 | 254.3 | 172.5 |
| Glycerol | 240.0 | 240.0 | 240.0 | 240.0 | 240.0 | 240.0 | 240.0 | 240.0 | 240.0 |
| Propylene glycol | 60.0 | 60.0 | 60.0 | 60.0 | 60.0 | 60.0 | 60.0 | 60.0 | 60.0 |
| Carbopol 934P | 10.0 | 10.0 | 10.0 | 10.0 | 10.0 | 10.0 | 10.0 | 10.0 | 10.0 |
| Triethanol-amine NF | 2.0 | 2.0 | 2.0 | 2.0 | 2.0 | 2.0 | 2.0 | 2.0 | 2.0 |
| Total | 1000.0 | 1000.08 | 1000.2 | 1000.4 | 1000.6 | 1000.83 | 1002 | 1004 | 1008.3 |

Table 8 shows further formulations, illustrating various solvent systems and where the concentration of glyceryl trinitrate is 0.05% by weight.

TABLE 8

| Ingredient | % by weight | | | |
|---|---|---|---|---|
| GTN 5% in EtOH | 1.00 | 1.00 | 1.00 | 1.00 |
| Ethanol | 33.02 | 31.00 | 33.02 | 33.02 |
| Glycerol | 30.00 | 10.00 | 30.00 | 24.00 |
| Water | 35.78 | 57.00 | 35.78 | 35.78 |
| Carbopol | 1.00 | 1.00 | 1.00 | 1.00 |
| Triethanolamine | 0.20 | 0.20 | 0.20 | 0.20 |
| Propyleneglycol | 0.00 | 0.00 | 0.00 | 6.00 |

The invention claimed is:

1. A spreadable gel or cream for topical application to a part of the body comprising a vasodilator as an active ingredient dissolved in a blend of volatile and non-volatile solvents of different solvating capacities for the active ingredient, wherein the volatile solvent comprises a mixture of water and a $C_1$-$C_5$ alcohol in a ratio by weight of 1.6:1 to 2.5:1, the non-volatile solvent comprises glycerol in a concentration from 5 to 40% by weight of the total solvent content, and the spreadable gel or cream comprises between 0.015 mg and 5 mg of glyceryl trinitrate in a unit-dosage form, wherein the concentration of the vasodilator present in the total solvent system is at or slightly below a saturated concentration such that super-saturation occurs upon loss of volatile components.

2. The spreadable gel or cream according to claim 1, wherein the alcohol comprises ethanol at a concentration up to 40% by weight.

3. The spreadable gel or cream according to claim 1, wherein the concentration of non-volatile solvent is 5 to 30%.

4. The spreadable cream or gel according to claim 1, wherein the non-volatile solvent further comprises a glycol.

5. A unit dosage form containing the spreadable gel or cream according to claim 1.

6. A kit comprising a composition according to claim 5 in an openable sealed container and instructions for use.

7. The spreadable gel or cream according to claim 1, wherein the volatile solvent is a mixture of water and ethanol in a ratio by weight of 1.6:1 to 2.5:1.

8. The spreadable gel or cream according to claim 5, wherein the concentration of glyceryl trinitrate is from 0.015 to 0.08% by weight.

9. The spreadable gel or cream according to claim 5, wherein the concentration of glyceryl trinitrate is from 0.0167 to 0.083% by weight.

10. The spreadable gel or cream according to claim 5, wherein the concentration of glyceryl trinitrate is from 0.04 to 0.08% by weight.

11. The spreadable gel or cream according to claim 1, wherein the alcohol has a maximum concentration of 40% by weight, based on the total formulation.

12. A sealed container containing the spreadable gel or cream according to claim 1.

* * * * *